United States Patent [19]
Cameron

[11] Patent Number: 5,295,992
[45] Date of Patent: Mar. 22, 1994

[54] PATELLA CUTTING SYSTEM
[75] Inventor: Michael J. Cameron, Warsaw, Ind.
[73] Assignee: Othy, Inc., Warsaw, Ind.
[21] Appl. No.: 851,504
[22] Filed: Mar. 16, 1992
[51] Int. Cl.[5] .............................................. A61B 17/16
[52] U.S. Cl. ..................................... 606/79; 606/80; 606/180; 128/751; 407/54; 407/61
[58] Field of Search .................... 606/79, 80, 81, 180; 128/751, 755, 756, 757; 407/61, 62, 63, 54, 34, 58, 59; 408/204, 206, 207, 703

[56] References Cited
U.S. PATENT DOCUMENTS

| | | | |
|---|---|---|---|
| 2,710,000 | 2/1952 | Cromer et al. | 606/180 |
| 3,880,546 | 4/1975 | Segal | 408/703 |
| 4,811,632 | 3/1989 | Salyer | |
| 5,100,267 | 3/1992 | Salyer | 407/54 |
| 5,116,165 | 5/1992 | Salyer | 407/54 |

Primary Examiner—C. Fred Rosenbaum
Assistant Examiner—N. Kent Gring
Attorney, Agent, or Firm—Lundy & Associates

[57] ABSTRACT

A tool having a shaft with a longitudinal axis and opposite ends. A boss is positioned at one of the ends. A tool collet is positioned at the other of the ends. A bore is in the boss end. The boss has a pair of pins that extend from opposite sides of the bore. A cutting lid with cutting edges on its top and a pair of bores passing therethrough. The cutting lid can be positioned on the pins and locked onto the boss, whereby upon rotation of the tool driver, the cutting lid is securely held in operable position on the tool driver throughout the operation and may be easily removed when desired.

19 Claims, 2 Drawing Sheets

5,295,992

PATELLA CUTTING SYSTEM

BACKGROUND OF THE INVENTION

The present invention pertains to holders for rotary tools and more particularly pertains to a tool cutting system particularly suitable for use with patella cutting blades or other similar tools.

Patella cutters are surgical tools which are used to mill the patella to accommodate the insertion of artificial knee joints. Patella cutting lids are mounted on tool drivers which in turn are mounted in the chuck or collet of a portable drill or flexible powered shaft. Patella cutting lids are separable from their tool drivers in order to be replaced or sharpened as they are used. It also may be necessary to change cutting lids during an operation. Tool drivers are relatively expensive, and thus must be cleaned and reused.

Some previous tool drivers grip the cutting lid by means of a flange and slot and an opposed spring loaded ball catch, like that on a socket wrench or socket driver, or other catch devices. This represents a problem in that the catch tends to trap dried blood and other debris, which is very difficult to remove during cleaning. An additional problem is that unless tolerances of cutting lids and tool drivers are made very close, there is considerable free play between the cutting lid and the tool driver. This increases wear and decreases the precision of the tool.

Additionally, the cutting lids being reused must be removed, cleaned, and sharpened as the cost in manufacturing and producing these highly sophisticated and reusable cutting lids is relatively great. There is also the accompanying cost of making the cutting lids aseptic for each operation.

Patella cutting systems cannot be compared with other surgical tools inasmuch as they are utilized to cut the patella, which together with the skull bone, is the hardest bone in the human body. Furthermore, in knee surgery, the patella must be cut leaving a flat, smooth surface within a relatively high tolerance. Additionally, the bone shavings cut from the patella need to be collected in some surgical techniques to be used in filling bone cavities formed by the surgery and enhancing healing. Because the patella is such a hard bone and patella cutters dull quickly during use, it is highly desirable to provide a patella cutting system in which the cutters are disposable, or if reusable, are easily resharpened, resterilized and reused relatively inexpensively.

The current cutting lids generally are not disposable. They must be cleaned and are costly to manufacture and produce. Additionally, because of their reusable character, there is always the chance that aseptic conditions of the operation are being compromised.

It is therefore highly desirable to provide an improved patella cutting system.

It is also highly desirable to provide an improved pin type tool driver which provides a locking means which can securely hold cutting lids.

It is also highly desirable to provide an improved cutting lid that is disposable.

It is also highly desirable to provide an improved patella cutting system that does not compromise the aseptic conditions of an orthopedic surgery procedure.

It is also highly desirable to provide an improved cutting lid that can be easily joined or disjoined from a tool driver.

It is also highly desirable to provide an improved patella cutting system that is less expensive to manufacture and produce.

It is also highly desirable to provide an improved patella cutting system which eliminates exposed parts which can catch and retain blood and other debris which present cleaning as well as sterilization problems.

It is finally highly desirable to provide an improved pin type tool driver and cutting lid which meet all of the above desired features.

SUMMARY OF THE INVENTION

It is an object of the invention to provide an improved patella cutting system.

It is also an object of the invention to provide an improved pin type tool driver which provides a locking means which can securely hold cutting lids.

It is also an object of the invention to provide an improved cutting lid that is disposable.

It is also an object of the invention to provide an improved patella cutting system that does not compromise the aseptic conditions of an orthopedic surgery procedure.

It is also an object of the invention to provide an improved cutting lid that can be easily joined or disjoined from a tool driver.

It is also an object of the invention to provide an improved patella cutting system that is less expensive to manufacture and produce.

It is also an object of the invention to provide an improved patella cutting system which eliminates exposed parts which can catch and retain blood and other debris which present cleaning as well as sterilization problems.

It is finally an object of the invention to provide an improved pin type tool driver and cutting lid which meet all of the above desired features.

In the broader aspects of the invention there is provided a tool having a shaft with a longitudinal axis and opposite ends. A boss is positioned at one of the ends. A tool collet is positioned at the other of the ends. A bore is in the boss end. The boss has a pair of pins that extend from opposite sides of the bore. A cutting lid with cutting edges on its top and a pair of bores passing therethrough. The cutting lid can be positioned on the pins and locked onto the boss, whereby upon rotation of the tool driver, the cutting lid is securely held in operable position on the tool driver throughout the operation and ma be easily removed when desired.

BRIEF DESCRIPTION OF THE DRAWINGS

The above mentioned and other features and objects of the invention and the manner of attaining them will become more apparent and the invention itself will be better understood by reference to the following description of an embodiment of the invention taken in conjunction with the accompanying drawings wherein.

DESCRIPTION OF A SPECIFIC EMBODIMENT

Figure 1:
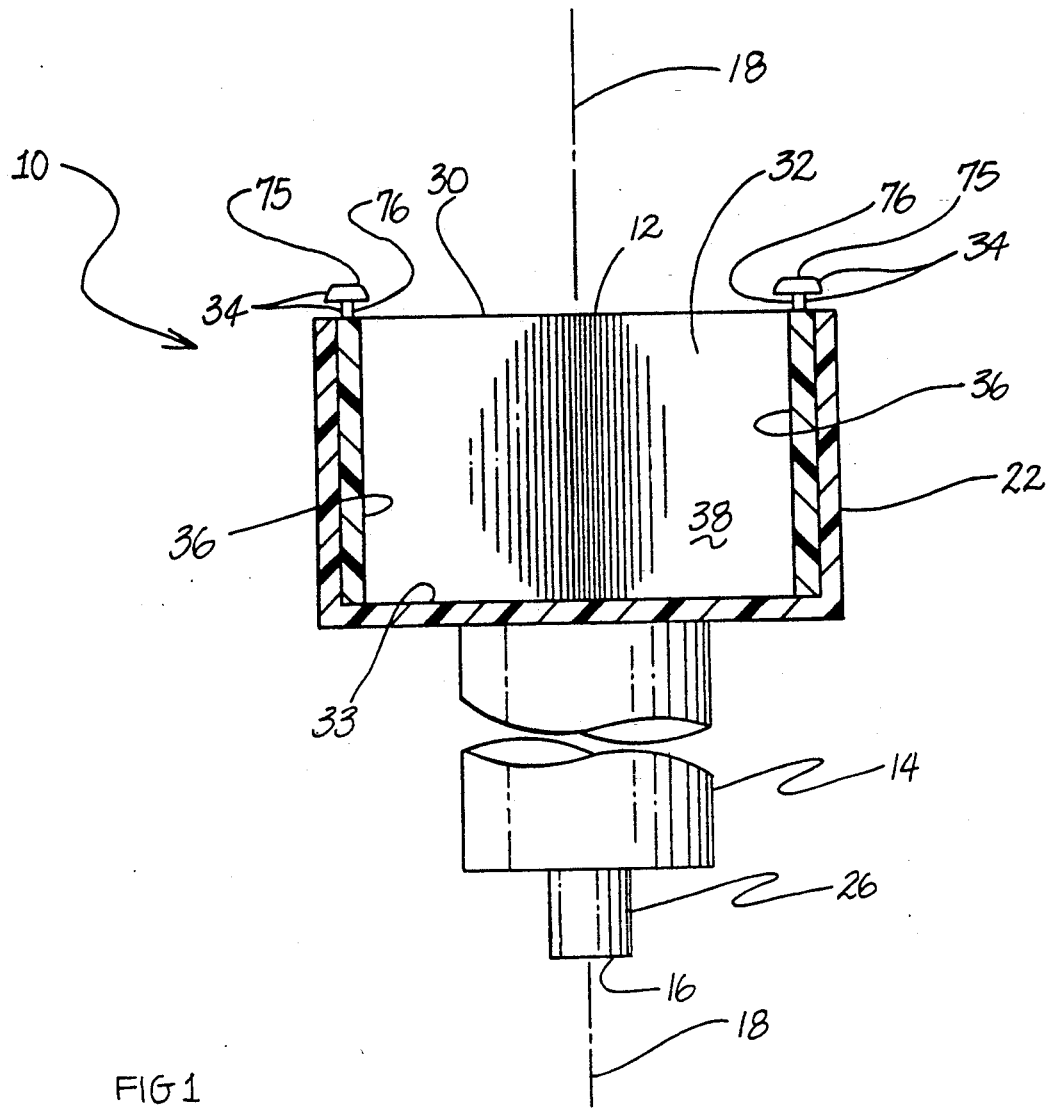
FIG. 1 is an axial cross-sectional plane view of the tool driver of the patella cutting system of the invention.

The patella cutting system of the invention includes a tool driver and a cutting lid. Tool driver 10 has a shaft 14 with a longitudinal axis 18 and opposite ends 12 and 16. At end 12 is located a boss 22. At end 16 is located a tool collet 26. Extending from end 12 axially of tool driver 10 is a bore 30 coaxial of boss 22. Bore 30 has a bottom 33 and upstanding walls 32. Bore 30 defines a debris cavity 38 which is coaxial of bore 30, boss 22 and shaft 14. Bottom 33 of bore 30 is shown to be flat, but other specific embodiments may be rounded or otherwise shaped so as to maximize the volume of hollow debris cavity 38 and to allow cavity 38 to be easily cleaned.

Figure 2:
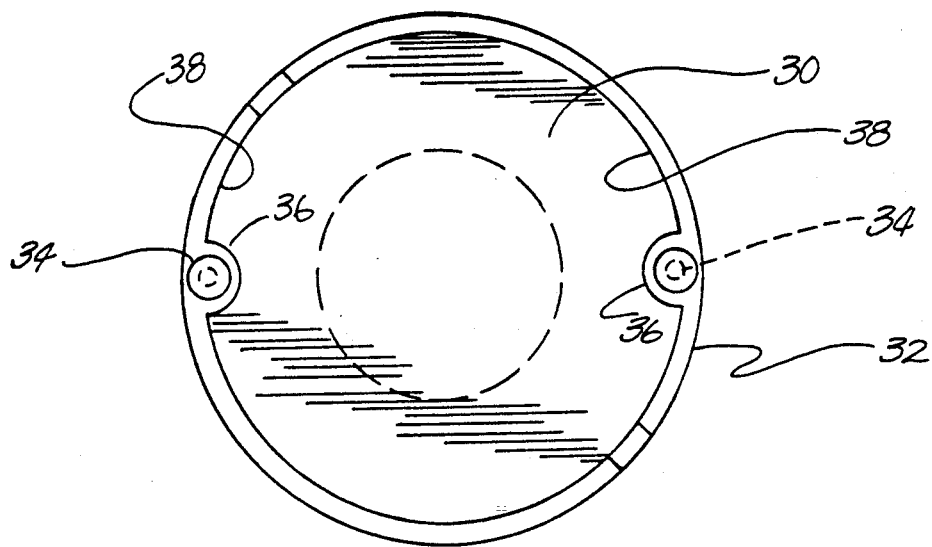
FIG. 2 is a top view of the tool driver of the patella cutting system of the invention as shown in FIG. 1.

Referring to FIGS. 1 and 2, boss 22 has a pair of pins 34 extending from boss 22 on opposite sides of bore 30. Pins 34 are parallel to axis 18 and equally spaced from axis 18. In the specific embodiment illustrated, pins 34 extend axially from pin supports 36 which extend the full depth of bore 30 axially of the tool driver 10. Alternatively, bore 30 is smaller or boss 22 is larger, thereby providing a wall thickness sufficient for pins 34 to extend from the wall defining bore 30, and pin supports 36 are eliminated.

Each of the pins 34 comprise a throat 76 and an enlarged head 75. Enlarged head 75 is spaced apart by throat 76 from end 12. In a specific embodiment, large headed screws positioned in threaded bores in pin supports 36 or boss 22 can be used instead of the pins 34 as shown.

Figure 6:
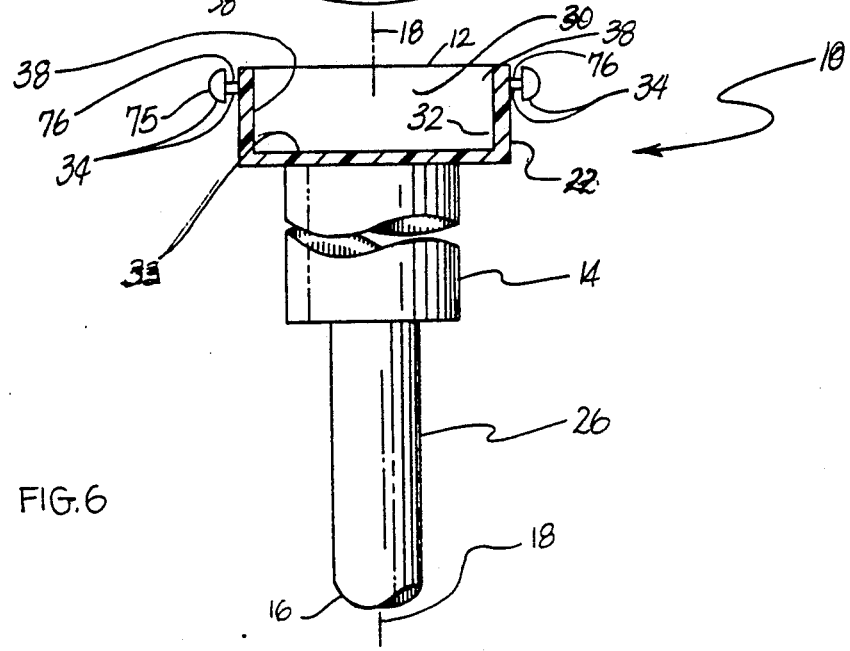
FIG. 6 is a perspective view of the cup cutting lid to be used with the tool driver shown in FIG. 5.

Referring to FIG. 6, in another specific embodiment, pins 34 extend from boss 22 on opposite sides of bore 30 transaxially. In this embodiment, pins 34 are positioned diametrically opposite. Pins 34 as above described, have throat portion 76 and enlarged head portion 75. Head portion 75 is spaced from boss 22.

Referring to FIGS. 1 through 4, a cutting lid 42 is provided for the tool driver 10. Cutting lid 42 has a top 46 and a bottom 50 and is provided with cutters 54 having cutting edges 58 and debris passages 70 rearwardly thereof. In the embodiment illustrated, cutting lid 42 is disk shaped.

Cutting lid 42 is attached to tool driver 10 by a first pair of bores 62 positioned diametrically opposite each other adjacent the periphery of cutting lid 42.

Figure 3:
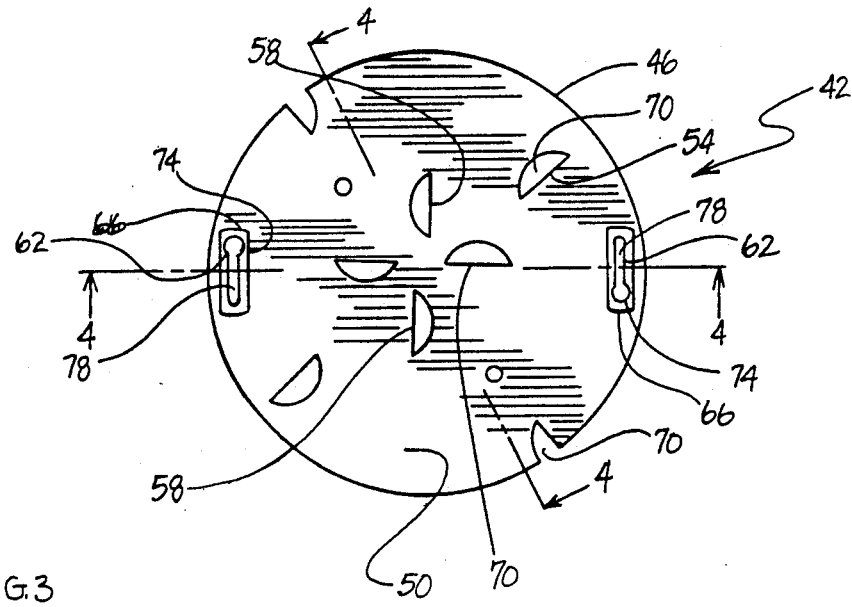
FIG. 3 is a top view of the cutting lid of the invention.

Each bore 62 has an enlarged portion 74 through which pin head 75 may pass and smaller portions 78 through which pin head 75 is too large to pass. Smaller portions 78 of bores 62 are sufficiently large to receive pin throat 76 therein. Cutting lid 42 may be secured to tool driver 10 by bores 62 by placing pins 34 therein. Pin head 75 may be passed through larger portions 74 and cutting lid 42 may be rotated with respect to tool driver 10 to position throat 76 within smaller bore portion 78. In this fashion, cutting lid 42 is secured in position on boss 22 of tool driver 10. Cutting lid 42 is provided with a plurality of cutters 54 having cutting edges 58 and debris passages 70 leading cutting edges 58. With reference to FIG. 3, and the rotation of the cutting lid 42 in a counter-clockwise direction, cutting lid edges 58 are always preceded by a debris passage 70 and the cutting resistance on cutting edges 58 urge throat 76 into smaller portion 78 of bores 62 thereby holding cutting lid 42 on boss 22 of tool driver 10, thus securing cutting lid 42 on boss 22 during use.

Upon completion of cutting, cutting lid 42 may be removed and cleaned or thrown away, as desired. For removal, cutting lid 42 is rotated relative to tool driver 10 and boss 22 to position throat 76 of pins 34 in enlarged portions 74 of bore 62. In this position, cutting lid 42 may be removed by separating the cutting lid 42 and the tool driver 10 axially.

Figure 5:
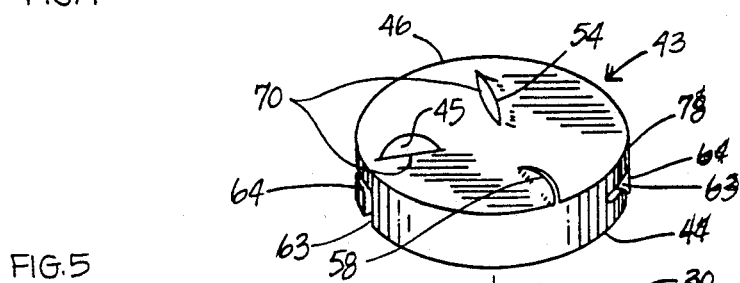
FIG. 5 is a view like FIG. 1 of yet another tool cutting system of the invention showing the pins extending transaxially from boss.

Referring to FIGS. 5 and 6 and the embodiment in which the pins 34 extend transaxially of bore 22, a cutting lid 43 is provided with a disk shaped top 46 and depending sides 44 thereby defining an interior 45. Cutting lid top 46 is, in all respects other than the bores 62, identical with the cutting lid 43. Sides 44 are provided with a pair of diametrically oppositely positioned bores 64 having access portions 63 which extend from the periphery of sides 44 to bores 64. In the specific embodiment shown in FIG. 6, bores 64 extend generally horizontally of the periphery of walls 44 and access portions 63 extend generally axially from the wall periphery to bores 64. Both bores 64 and access portions 63 have a size larger than throat 76, but smaller than pin head 75 of pins 34. Cutting lid 43 may be positioned on boss 22 by positioning throat 76 within access portions 63 of bores 64 and moving cutting lid 43 axially of boss 22 so as to move throat 76 toward bores 64, and then rotating cutting lid 43 about axis 18 so as to position throat 76 in bores 64. In the specific embodiment shown in FIGS. 5 and 6, the rotation of cutting lid 43 with respect to tool driver 10 will be counter-clockwise to lock cutting lid 43 onto tool driver 10.

Similarly, cutting lid 43 may be removed from tool driver 10 upon the completion of cutting and cleaned or thrown away. For removal, cutting lid 43 is rotated relative to tool driver 10 to position throat 76 of pins 34 in access portions 63 and bores 64 and separating cutting lid 43 axially of tool driver 10 thereby moving throat 76 through access portions 63 until cutting lid 43 is separated from tool driver 10.

Both cutting lid 42 and top 46 of cup cutting lid 43 have a plurality of cutting edges 58 positioned thereon. Cutting edges 58, in the specific embodiment shown, are straight and generally parallel to the top of cutting lids 42 and 43. Cutting edges 58 are each generally radial of cutting lids 42 and 43. Further, cutting edges 58 are each positioned to extend over the entire surface of cutting lids 42 and 43. In a specific embodiment such as shown in FIG. 3, there are two cutting edges 58 in diametrically opposite positions which cover the same territory. Cutting edges 58 are also positioned to overlap each other. In a specific embodiment, the overlap is about fifty percent of the length of the cutting edges 58.

Each of the cutting edges 58 are preceded by a debris passage 70. The specific purpose of these debris passages 70 will be mentioned hereinafter. In the specific embodiment shown, each debris passage 70 is semi-circular in shape. However, in other embodiments, these debris passages 70 may be rectangular, square, or shaped as otherwise desired. In a specific embodiment, cutting edges 58 are equally spaced over cutting lid 42 and top 46 of cutting lid 43. In the specific embodiment illustrated in FIG. 3, each cutting edge 58 is positioned on a radii about 45° apart from adjacent cutting edges 58.

Cutting edges 58 each are spaced from top 46 of cutting lids 42 and 43. In a specific embodiment, this spacing of the cutting edge is about 0.03 inches.

Figure 4:
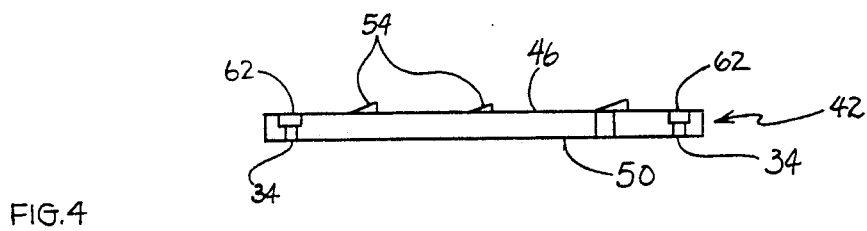
FIG. 4 is a cross-sectional view of the cutting lid of FIG. 3 taken substantially along line 4—4 of FIG. 3.

In a specific embodiment, cutting lid 42 has milled portions 66 recessed around bores 62. Milled portions 66 allow enlarged pin heads 75 to be flush with top 46 of cutting lid 42 as shown in FIG. 4. In a specific embodiment, milled portions 66 are tapered with respect to bottom 50 from smaller portions 78 towards larger portions 74 of bores 62 such that movement of throat 76 of pins 34 from enlarged portions 74 into smaller portions 78 will urge cutting lid 42 against end 12 and boss 22 of tool driver 10.

Similarly, in a specific embodiment of the cutting lid 43, bores 64 may be angled with respect to bottom 50 and the periphery of sides 44 so as to urge cup cutting lid 43 onto end 12 and boss 22 upon the movement of throat 76 of pins 34 into bores 64.

In operation, the tool driver 10 is placed in the chuck of a conventional drill or driver (not shown). The tool driver 10 is rotated counter-clockwise. The Cutting lid 42 is positioned on the tool driver 10. The cutting lid 43 is positioned on the tool driver 10 in a similar fashion with the cutting lids positioned on the tool driver 10, the tool driver 10, cutting lids 42 and 43, the boss 22, the shaft 14, and the tool collet 26 all rotate about longitudinal axis 18. Inasmuch as all of the cutting edges 58, pins 34, milled portions 66, bores 62, bores 64, and debris passages 70 are each provided in pairs positioned on diameters of cutting lids 42 and 43 equally spaced from the center thereof, cutting lids 42 and 43, boss 22 and tool driver 10 are each balanced about axis 18 such that when rotated about axis 18, no vibration occurs.

The patella cutting system is utilized to shave bone from the inside of the patella when operating on the knee of a person. Debris cut from the patella by the cutting edges 58 pass through the debris passages 70 and are deposited within the debris cavity 38. At various times during the operation, cutting lids 42 and 43 may be removed and the debris may be removed from debris cavity 38 and a new cutting lid 42 or 43 may be positioned as above described on tool driver 10. This may occur several times during a single operation inasmuch as the patella is one of the hardest bones of the human body. The bone debris cut from the patella by the patella cutting system of the invention is saved to be later used during the operation in accordance with standard surgical procedures.

When the cutting lids 42 and 43 are desirably removed from the tool driver 10, tool driver 10 is stopped from rotation and the cutting lids 42 and 43 are rotated with respect to the tool driver 10 in a clockwise direction moving the pins 34 into enlarged portions 63 and 74. In this position, cutting lids 42 and 43 may be separated from the tool driver 10 by moving them apart axially.

Cutting lids 42 and 43 can be cleaned, sharpened and reused or discarded as the case may be. The disk shape of the cutting lid 42 allows cutting lid 42 to be manufactured relatively inexpensively and, in many instances, be disposable. Disposability of cutting lid 42 allows for cutting lid 42 to be furnished to surgeons in a sterile pack, thereby eliminating concern over the desired aseptic conditions of the operating room.

The fact that the heads 75 of the pins 34 are flush with top 46 of the cutting lid 42 positions cutting edges 58 as those portions in contact with the patella during use. Inasmuch as the heads 75 of pins 34 are recessed from the top 46 of cutting lid 42, there is no chance for the heads 75 to contact the patella or to gouge the same. Thus, the patella may be left with a smoothly cut, essentially planar surface utilizing both the cutting lids 42 and 43. With the cutting edges 58 covering the total surface area top 46 upon the rotation of the invention, the improved patella cutting system improves upon the cutting tolerances. Heretofore, normal tolerances were about 0.030 inches. Cutting tolerances with the improved patella cutting system of the invention are within 0.010 inches.

By the invention, an improved patella cutting system is provided. The improved patella cutting system provides a means by which both cutting lids 42 and 43 can be securely held on the tool driver 10. The cutting lids may be disposable if desired. By the cutting lids being disposable, the aseptic conditions of an orthopedic surgery procedure need not be compromised. Both cutting lids 42 and 43 can be easily joined or disjoined to the tool driver 10 with a single hand. The improved patella cutting system can be manufactured less expensively than those proposed heretofore and can be cleaned and sterilized, easily.

While a specific embodiment of the invention has been shown and described herein for purposes of illustration, the protection afforded by any patent which may issue upon this application is not strictly limited to the disclosed embodiment; but rather extends to all structures and arrangements which fall fairly within the scope of the claims which are appended hereto:

What is claimed is:

1. A patella cutting tool comprising a shaft having a longitudinal axis and opposite ends, a boss at one of said ends, a tool collet at the other of said ends, a bore on said boss extending axially of said shaft, a pair of pins extending from said boss on opposite sides of said bore, a cutting lid, said cutting lid having a top and a bottom, said top of cutting lid having cutters with cutting edges extending from said top, a pair of first bores extending through said cutting lid, said pins in said bores and a lock, said cutting edges being staggered to cover the entire area of said top, said lid having debris passages therein whereby said cutting lid may be retained on said boss and securely fastened to said shaft and the cuttings collected in said bore.

2. The tool of claim 1 wherein said cutting edges are substantially parallel to said top of said cutting lid and are disposed to cut upon rotation of said shaft.

3. The tool of claim 1 wherein said cutting edges are spirally arranged.

4. The tool of claim 1 wherein said cutting edges upon rotation of said cutting lid about said axis each sweep an area overlapped by other of said cutting edges a total of about one and one-half times.

5. The tool of claim 1 wherein said lock comprises said pins having enlarged distal ends and throat, said bores having an enlarged portion and a smaller portion, said enlarged portion being larger than said distal ends, said smaller portion being larger than said throat and smaller than said distal ends, whereby said distal ends may be passed through said enlarged portion and said lid rotated with respect to said boss positioning said throat in said smaller portions.

6. The tool of claim 1 wherein said lock comprises at least a pair of screws extending through said lid into said bores.

7. A patella cutting tool comprising a shaft having a longitudinal axis and opposite ends, a boss at one of said ends, a tool collet at the other of said ends, a bore in said boss extending axially of said shaft, a pair of oppositely disposed pins extending from boss on opposite sides of said bore, a cutting lid, said cutting lid having a top and a bottom, said top of said cutting lid having cutters with cutting edges extending from said top, a pair of first bores oppositely disposed and extending through said cutting lid, said pins in said bores, said cutting edges being staggered to cover the entire area of said top, said lid having debris passages therein, said cutting edges each sweep an area overlapped by other of said cutting edges the total of about one and one-half times, said cutting edges being substantially parallel to said top of said cutting lid, said pins having enlarged distal ends and throat, said bores having an enlarged portion and a smaller portion, said enlarged portion being larger than said distal ends, said smaller portion being larger than said throat and smaller than said distal ends.

8. The tool of claim 7 wherein said cutting lid is disk shaped.

9. The tool of claim 7 wherein said lock comprises at least a pair of screws extending through said lid into said pair of bores.

10. The tool of claim 7 wherein said cutting lid is disposable.

11. The tool of claim 7 wherein said cutters extend from said top of said cutting lid angular to said axis a height of about 0.03 inches, said cutting edges being parallel to said cutting lid having length of about 0.25 inches whereby said tool resists blunting and cuttings can be collected in said bore.

12. The tool of claim 7 wherein said cutting lid has sides.

13. The tool of claim 7 wherein said pins extend from said boss transaxial of said axis and on opposite sides of said bore whereby said cutting lid may be securely fastened to said boss and cuttings can be collected in said bore of said shaft.

14. The tool of claim 7 wherein said cutting edges are radial of said lid.

15. The tool of claim 7 wherein said cutting edges are on radii about 45° apart.

16. A patella cutting tool comprising a shaft having a longitudinal axis and opposite ends, a boss at one of said ends, a tool collet at the other of said ends, a bore in said boss extending axially of said shaft, a pair of pins extending from said boss on opposite sides of said bore, a cutting lid, said cutting lid having a top and a bottom, said top of said cutting lid having cutters with cutting edges extending from said top, a pair of first bores extending through said cutting lid, said pins in said bores and a lock on said pins, said cutting edges being staggered to cover the entire area of said top, said lid having debris passages therein, said cutting edges being substantially parallel to said top of said cutting lid and disposed to cut upon rotation of said shaft, said cutting edges being spirally arranged, said cutting edges upon rotation of said cutting lid about said axis each sweep an area overlapped by other of said cutting edges a total of about one and one-half times, said cutting edges being radial of said lid.

17. A patella cutting tool comprising a shaft having a longitudinal axis and opposite ends, a boss at one of said ends, a tool collet at the other of said ends, a bore in said boss extending axially of said shaft, a pair of pins extending from said boss on opposite sides of said bore, a cutting lid, said cutting lid having a top and a bottom, said top of said cutting lid having cutters with cutting edges extending from said top, a pair of first bores extending through said cutting lid, said pins in said bores and a lock on said pins, said cutting edges being staggered to cover the entire area of said top, said lid having debris passages therein, said cutting lid being disk shaped, said cutters extending from said top of said cutting lid angular to said axis a height of about 0.03 inches, said cutting edges being parallel to said cutting lid having length of about 0.25 inches, said cutting edges are radial of said lid, said cutting edges are on radii of about 45° apart.

18. The tool of claim 17 wherein said cutting edges are radial of said lid.

19. The tool of claim 17 wherein said cutting edges are on radii about 45° apart.

* * * * *